United States Patent [19]
Woodle et al.

[11] Patent Number: 5,998,687
[45] Date of Patent: Dec. 7, 1999

[54] ETHYLBENZENE PROCESS USING STACKED REACTOR LOADING OF BETA AND Y ZEOLITES

[75] Inventors: Guy B. Woodle, Mount Prospect, Ill.; Alan E. Cepla, Woodham, United Kingdom

[73] Assignee: UOP LLC, Des Plaines, Ill.

[21] Appl. No.: 09/124,555

[22] Filed: Jul. 29, 1998

Related U.S. Application Data

[60] Provisional application No. 60/053,834, Jul. 29, 1997.

[51] Int. Cl.$^6$ ................... C07C 2/64; C07C 2/68
[52] U.S. Cl. ........................... 585/449; 585/467
[58] Field of Search .................... 585/449, 467, 585/323

[56] References Cited

U.S. PATENT DOCUMENTS

| | | | |
|---|---|---|---|
| 3,130,007 | 4/1964 | Breck | 23/113 |
| 3,929,672 | 12/1975 | Ward | 252/455 Z |
| 4,028,227 | 6/1977 | Gustafson | 208/216 |
| 4,185,040 | 1/1980 | Ward et al. | 585/467 |
| 4,798,816 | 1/1989 | Ratcliffe et al. | 502/62 |
| 4,891,458 | 1/1990 | Innes et al. | 585/323 |
| 5,003,119 | 3/1991 | Sardina et al. | 585/323 |
| 5,081,323 | 1/1992 | Innes et al. | 585/449 |
| 5,522,984 | 6/1996 | Gajda et al. | 208/120 |
| 5,723,710 | 3/1998 | Gajda et al. | 585/467 |

OTHER PUBLICATIONS

H.U. Hammershaimb et al. "Alkylation" in: *Encyclopedia of Chemical Technology* (1992 ed.), vol. 2, pp. 85–112. Ref. TP9.E685.

*Primary Examiner*—Glenn Caldarola
*Assistant Examiner*—Thuan D. Dang
*Attorney, Agent, or Firm*—Thomas K. McBride; John G. Tolomei; Michael A. Moore

[57] ABSTRACT

Benzene is catalytically alkylated with ethylene in a process which comprises at least two catalyst zones. Benzene and ethylene contact a catalyst comprising zeolite beta in a first catalyst zone. Ethylene and the effluent from the first catalyst zone contact a catalyst comprising zeolite Y to produce an alkylate containing ethylbenzene.

13 Claims, 5 Drawing Sheets

5,998,687

ETHYLBENZENE PROCESS USING STACKED REACTOR LOADING OF BETA AND Y ZEOLITES

CROSS-REFERENCE TO RELATED APPLICATION

This application claims the benefit of U.S. provisional application No. 60/053,834, filed on Jul. 29, 1997.

FIELD OF THE INVENTION

This invention relates to the production of ethylbenzene by the reaction of benzene and ethylene.

BACKGROUND OF THE INVENTION

The alkylation of aromatic hydrocarbons such as benzene using solid catalyst is a well-developed art which is practiced commercially in large scale industrial units. One commercial application of this process is the alkylation of benzene with ethylene to produce ethylbenzene, which is subsequently used to produce styrene. The basic configuration, general design, and operation of a catalytic alkylation process to produce ethylbenzene are known in the art. Benzene and ethylene gas pass to an alkylation zone containing generally two or more, and typically from two to six, beds of catalyst in series. Suitable cooling means may be provided between catalyst beds to compensate for the net exothermic heat of reaction in each of the catalyst beds. The net effluent of the beds passes to a separation zone, usually comprising one or more distillation columns, which recover ethylbenzene while recycling benzene and rejecting by-products.

The performance of ethylbenzene processes is influenced by the selectivity and activity of the catalyst in the operating environment of the process. Currently available catalysts for the alkylation of benzene with ethylene include aluminum chloride catalysts and zeolite-containing catalysts. Zeolitic catalysts have certain advantages, such as fewer problems with corrosion and with disposal of spent catalyst, over aluminum chloride catalysts. But, despite these clear advantages, zeolitic catalysts generally produce the same amount of polyethylated benzene by-products as aluminum chloride catalysts. Thus, the goal of minimizing the formation of polyethylbenzenes by maximizing the efficient use of ethylene is a driving force for further developments in zeolitic catalysis for ethylbenzene processes.

The formation of some polyethylbenzenes, such as diethylbenzenes and triethylbenzenes, does not necessarily, however, represent a reduction in the efficient use of ethylene, because diethylbenzenes and triethylbenzenes each can be readily transalkylated by benzene to produce ethylbenzene. In contrast to diethylbenzenes and triethylbenzenes, however, other by-products, which are collectively referred to as flux oil, do represent a reduction in ethylene utilization and a loss of ethylene.

Flux oil is a recognized term in the art of aromatic alkylation. Flux oil is an alkylation by-product that is generally formed by polyalkylation of benzene or by alkylation of benzene with substituted benzene by-products. As such, flux oil may have a variety of different compositions and physical properties depending on the reactants charged to the alkylation process, the alkylation catalyst, the alkylation operating conditions, etc. The composition and properties of the flux oil will also depend on whether a separate transalkylation zone is present, and if such a transalkylation zone is present, on the transalkylation catalyst, the transalkylation conditions, etc.

Flux oil is the highest-boiling fraction of the alkylation reactor effluent that is not recycled to either alkylation or transalkylation in order to produce the desired product. Flux oil is usually obtained by distilling from the alkylation reactor effluent the desired product and all of the recyclable by-products. The low end of the boiling range of flux oil is normally the boiling point of the lightest by-product that does not readily alkylate or transalkylate to produce the desired product. Thus, flux oil contains by-products that do not readily alkylate or transalkylate to produce the desired product, as well as other by-products that can alkylate or transalkylate to produce the desired product but which can not be readily separated by distillation from by-products that do not readily alkylate or transalkylate to produce the desired product. As used herein, components that can not be readily separated by distillation are components that have distillation points that differ by less than 10° F. (5° C.). For example, in ethylbenzene processes flux oil generally includes 1,1-diphenylethane (1,1-DPE) and alkylated 1,1-diphenylethanes which can not be converted to ethylbenzene by transalkylation. But, flux oil in ethylbenzene processes also generally includes heavy polyethylbenzenes, such as tetraethylbenzenes, pentaethylbenzene, and hexaethylbenzene, which can transalkylate to ethylbenzene but which can not be readily separated by distillation from 1,1-diphenylethane or alkylated derivatives thereof. In fact, the by-production of the heavier polyethylbenzenes other than diethylbenzenes and triethylbenzenes and of 1,1-DPE, which are major components of flux oil in ethylbenzene processes, represents virtually all of the reduction in ethylene utilization.

Thus, in order to maximize ethylene utilization and minimize ethylene losses in the production of ethylbenzene, there is a need for a process that minimizes the production of flux oil.

SUMMARY OF THE INVENTION

This invention is an improved method of producing ethylbenzene by alkylating benzene with ethylene in the presence of a zeolitic catalyst.

It is an object of the present invention to provide an improved process for the alkylation of benzene with ethylene in the presence of a zeolitic catalyst. Another objective of this invention is to decrease the yield of flux oil by-product from the alkylation of benzene with ethylene.

This invention is based on the discovery that a two-catalyst-zone alkylation process employing a first catalyst comprising a zeolite beta and a second catalyst comprising a zeolite Y demonstrates surprising yield improvements over a single-catalyst-zone system of either zeolite beta or zeolite Y.

Although this invention is not limited by any particular theory, it is believed that part of the explanation for the surprising yield improvements may lie in an unexpected difference between zeolite beta and zeolite Y in the manner in which flux oil production varies with alkylation temperature. It has now been observed that the yield of flux oil increases as temperature increases for a catalyst containing zeolite beta, whereas the flux oil yield decreases as temperature increases for a catalyst containing zeolite Y. On the one hand, then, this invention can be considered to be a process that takes advantage of this unexpected difference in the temperature dependency of flux oil make, particularly in an adiabatic reactor. The reason for this is that alkylation reactions are moderately exothermic, and therefore placing zeolite beta in the front of an adiabatic alkylation reactor where the temperature is relatively low, and placing zeolite Y in the back where the temperature is relatively high, puts each zeolite in its optimum temperature environment for minimizing production of flux oil. On the other hand, the explanation for the surprising yield improvements may not lie in the temperature dependency of flux oil, but rather in the relative ability of zeolite Y catalyst, as compared to zeolite beta catalyst, to process a feed stream containing the effluent of another alkylation bed. Whatever the explanation, this invention is a two-catalyst zone alkylation process that employs beta in the first zone and Y in the second zone, and this invention is not limited to any particular theory.

In addition to the surprisingly improved yields, this invention is expected to provide another benefit, namely longer catalyst life, especially where the zeolite beta catalyst operates at a lower temperature than the zeolite Y catalyst. Generally, in the catalytic alkylation of benzene with ethylene, a decrease in alkylation temperature increases the tendency of high-molecular weight intermediates and by-products to remain on the surface of the catalyst, thereby deactivating the catalyst more rapidly. Thus, in a two-bed reactor with each bed containing the same catalyst but operating at two different temperatures, the catalyst in the bed that operates at the lower temperature tends to deactivate more rapidly than the catalyst in the bed that operates at the higher temperature. But, zeolite beta catalyst generally has a slower deactivation rate than zeolite Y catalyst. Accordingly, in one embodiment this invention compensates for the tendency of the low-temperature bed to deactivate more rapidly than the high-temperature bed by placing the zeolite beta catalyst in the low-temperature bed and the zeolite Y catalyst in the high-temperature bed. This is because placing the catalyst that has a slower deactivation rate (i.e., beta) in the low-temperature bed tends to offset the fact that the low-temperature bed would otherwise deactivate more rapidly. Consequently, such embodiments of this invention are expected to exhibit improved catalyst life.

One broad embodiment of the present invention is a process for producing ethylbenzene. A first feed comprising benzene and ethylene contacts with a first catalyst comprising zeolite beta in a first catalyst zone, which operates at first alkylation conditions. A first effluent is obtained from the first catalyst zone. A second feed, which includes at least a portion of the first effluent, comprises ethylene and benzene. The second feed contacts a second catalyst comprising zeolite Y in a second catalyst zone, which operates at second alkylation conditions. A second effluent comprising ethylbenzene is obtained from the second catalyst zone.

INFORMATION DISCLOSURE

Figure 1:
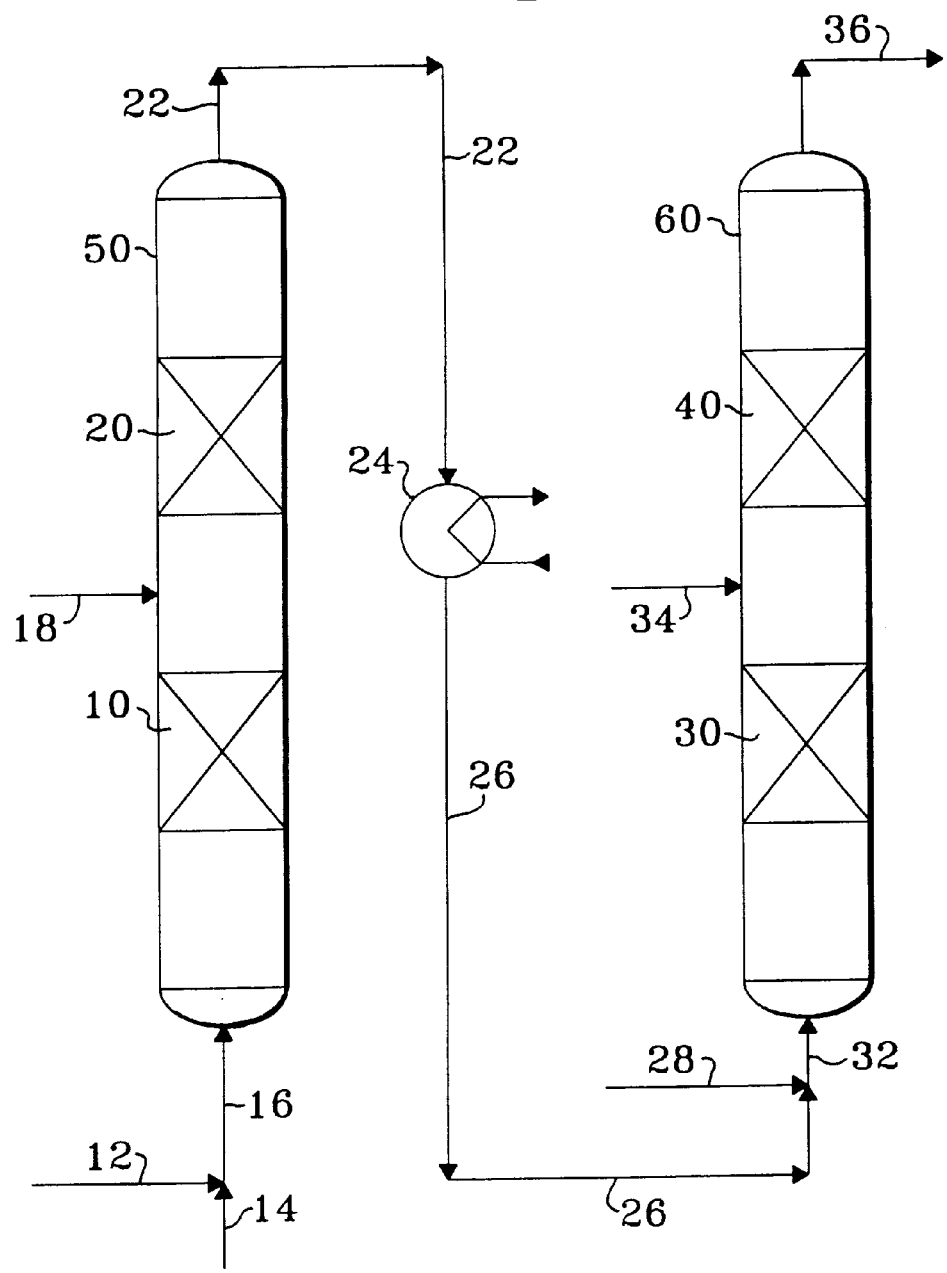
FIG. 1 shows an embodiment of the present invention.

Catalytic alkylation process to produce ethylbenzene are known in the art and are taught, for example, in the article written by H. U. Hammershaimb, et al., entitled "Alkylation," which appears at pages 85–112 in *Kirk-Othmer Encyclopedia of Chemical Technology*, Fourth Edition, Volume 2, edited by J. I. Kroschwitz et al., published by John Wiley and Sons, New York, in 1992.

U.S. Pat. Nos. 3,130,007 and 3,929,672 disclose zeolite Y suitable for alkylating benzene with ethylene. The teachings of U.S. Pat. Nos. 3,130,007 and 3,929,672 are incorporated herein by reference.

U.S. Pat. Nos. 4,028,227 and 4,185,040 teach catalyst particles in a tri-lobe shape. The teachings of U.S. Pat. Nos. 4,028,227 and 4,185,040 are incorporated herein by reference.

U.S. Pat. No. 4,798,816 discloses a process for treating a zeolite-containing alkylation catalyst in a manner that produces high yields of monoalkylated aromatic products.

U.S. Pat. Nos. 4,891,458, 5,081,323, and 5,522,984 teach zeolite beta for use as alkylation catalysts. The teachings of U.S. Pat. Nos. 4,891,458, 5,081,323, and 5,522,984 are incorporated herein by reference.

DETAILED DESCRIPTION OF THE INVENTION

In accord with this invention, the individual first and second catalyst zones respectively containing the first and second zeolitic catalysts are typically located in separate beds in a single reactor, although it is possible that the catalyst zones could be located in separate reactors. Each catalyst zone may be located in two or more reactors with suitable cooling means provided between reactors, for example, with the first catalyst zone located in the first reactor and the second catalyst zone in two or three subsequent reactors. However, this invention is not limited to processes either that do or do not use interstage cooling, that do or do not use interstage quenching, or that do or do not operate with the second catalyst zone at a higher, lower, or the same temperature as the first catalyst zone. The segregated catalyst zones also may be separated by one or more reaction zones containing a catalyst having a different composition from either of the catalysts in the two zones of the present invention.

The first catalyst, or the zeolite beta component thereof, comprises generally from about 10% to about 90%, and preferably from about 20% to about 70%, of the total quantity (by mass or by volume) of catalyst, or of zeolite, in all of the catalyst zones. The second catalyst, or the zeolite Y component thereof, generally comprises from about 10% to about 90%, and preferably from about 30% to about 80%, of the total quantity (by mass or by volume) of catalyst, or of zeolite, in all of the catalyst zones.

The reactants may contact the catalyst in individual reactors in either upflow, downflow, or radial-flow fashion, with the upflow mode being preferred. The catalyst is contained in a fixed-bed system or a moving-bed system, but the preferred embodiment of the current invention is a fixed-bed system. Various approaches to reactivation of the catalyst are possible, with the preferred approach being the semiregenerative approach, that is, the entire unit is operated to maintain activity by gradually increasing temperature to maintain product quality, finally shutting the unit down for catalyst regeneration and reactivation. An alternative approach to reactivation is the swing reactor approach, in which individual reactors are individually isolated by manifolding arrangements as the contained catalyst becomes deactivated, and the catalyst in the isolated reactor is regenerated and reactivated while the other reactors remain on-stream. The appropriate mode depends on individual circumstances, e.g., the configuration of an existing unit in which the invention is to be used. For a new unit, the choice would be determined by such factors as the importance of yield, desired on-stream efficiency, and capital cost.

Effluent from the alkylation zone is passed through a heating means to a separation zone, which typically comprises a number of separation stages to separate the desired ethylbenzene product from by-products and from excess benzene. The present invention may use any combination of columns and separators to recover ethylbenzene and, if desired, to produce streams of benzene and polyethylbenzenes.

The feedstocks that are charged to the present alkylation process contain benzene and ethylene. The benzene-containing feedstock may comprise other aromatic hydrocarbons, including alkylbenzenes such as ethylbenzene, polyethylbenzenes, butylbenzenes, polybutylbenzenes, and alkylated benzenes having at least one ethyl group and at least one butyl group, diphenylethanes, ethyldiphenylethanes, or polyethyldiphenylethanes. The ethylene-containing feedstock may comprise other light olefins such as propylene and light paraffins such as ethane and propane.

First and second alkylation conditions used in each of the catalyst zones of the present alkylation process include a molar ratio of phenyl groups per ethyl group of from 25:1 to about 1:1. The molar ratio may be less than 1:1, and it is believed that the molar ratio may be 0.75:1 or lower. The molar ratio of phenyl groups per ethyl group, which is sometimes referred to as the phenyl/ethyl ratio, is a key operating variable in ethylbenzene alkylation. The numerator of this ratio is the number of moles of phenyl groups passing through the alkylation zone during a specified period of time. The number of moles of phenyl groups is the sum of all phenyl groups, regardless of the compound in which the phenyl group happens to be. For example, one mole of benzene, one mole of ethylbenzene, and one mole of diethylbenzene each contribute one mole of phenyl group to the sum of phenyl groups. The denominator of this ratio is the number of moles of ethyl groups passing through the alkylation zone during the same specified period of time. The number of moles of ethyl groups is the sum of all ethyl and ethenyl groups, regardless of the compound in which the ethyl or ethenyl group happens to be. For example, one mole of ethylene and one mole of ethylbenzene each contribute one mole of ethyl group to the sum of ethyl groups, whereas one mole of diethylbenzene contributes two moles of ethyl groups.

The molar ratio of phenyl groups to ethyl groups affects the rise in temperature in the first or second catalyst zone that occurs as a result of the alkylation reactions. The alkylation reactions have a heat of reaction of 100–150 BTU/lb-mole and are considered to be moderately exothermic. Although some ethylbenzene reactors have indirect heat exchange means to remove the heat as it is produced, most ethylbenzene reactors are adiabatic, and so the outlet temperature of the effluent stream is higher than the inlet temperature of the reactants. An increase in the molar ratio of phenyl groups to ethyl groups in the feed stream increases the quantity of phenyl groups available to act as a heat sink in the catalyst zone and thus decreases the temperature rise in the catalyst zone. Accordingly, in practicing this invention, the inlet temperature in the first catalyst zone is generally from 392 to 500° F. (200 to 260° C.), and preferably from 410 to 446° F. (210 to 230° C.). Although the temperature rise that occurs in the catalyst zone could be as high as 342° F. (190° C.) depending on the total mass flows in the reactor, the temperature rise is generally from 9 to 90° F. (5 to 50° C.), and preferably from 9 to 54° F. (5 to 30° C.). The alkylation temperature in second catalyst zone is generally at least 45° F. (25° C.), and more preferably from 45 to 54° F. (25 to 30° C.), greater than the alkylation temperature in the first catalyst zone. In general, the appropriate reaction temperature is generally from 212° F. (100° C.) to at least the critical temperature of benzene, which is 552° F. (289° C.), or even higher. However, if the alkylation conditions occur at least partially in the vapor phase, the reaction temperature could be as high as 900° F. (482° C.).

As described previously, the temperature rise in the catalyst zone may be controlled by adjusting the molar ratio of phenyl groups to ethyl groups in the feed stream. Minimizing the temperature rise helps prevent high reactor outlet temperatures, which cause undesirable side reactions such as cracking of hydrocarbons to occur. High reaction temperatures can also cause vaporization of benzene and ethylbenzene in the catalyst zone.

Although it is believed that the first and second catalyst zones could operate in the vapor phase, the first and second alkylation conditions are preferably such that alkylation is performed in the liquid phase. Consequently, reaction pressure needs to be sufficiently high to ensure at least a partial liquid phase. Where ethylene is the olefin, the pressure range for the first or second catalyst zone is usually from about 200 to about 1000 psi(g) (1379 to 6985 kPa(g)), more commonly from about 300 to about 600 psi(g) (2069 to 4137 kPa(g)), and even more commonly from about 450 to about 600 psi(g) (3103 to 4137 kPa(g)). Preferably, the reaction conditions are sufficient to maintain benzene in a liquid phase and are supercritical conditions for ethylene. Pressure in the first or second catalyst zone is not a critical variable in the success of this invention, however, and the only criterion is that the pressure be sufficiently great to ensure at least partial liquid phase. The weight hourly space velocity of ethylene in the first or second catalyst zone may range from 0.01 to 2.0 $hr^{-1}$. The weight hourly space velocity of aromatics, including benzene, in the first or second catalyst zone is generally from 0.3 to 480 $hr^{-1}$.

The ethylene-containing feedstock may be injected into both the first and second catalyst zones or into only the first catalyst zone. Where the ethylene-containing feedstock is injected into both the first and second catalyst zones, the portion of ethylene-containing feedstock that passes to the first catalyst zone is generally from 20% to 95% of the total ethylene-containing feedstock that passes to both the first and second catalyst zones. The remainder, which in this most general case is from 5% to 80% of the total ethylene-containing feedstock, passes to the second catalyst zone. More preferably, from 50% to 90% of the total ethylene-containing feedstock passes to the first catalyst zone and from 10% to 50% of the total passes to the second catalyst zone. Even more preferably, from 60% to 80% of the total passes to the first catalyst zone and from 20% to 40% of the total passes to the second catalyst zone. Most preferably, 67% of the total passes to the first catalyst zone and 33% passes to the second catalyst zone. Although equal amounts of the ethylene-containing feedstock may be passed to the first and second catalyst zones, the advantage of passing more than 50% of the ethylene-containing feedstock to the first catalyst zone is that the selectivity toward mono-ethylated benzenes, as opposed to poly-ethylated benzenes, increases. On the other hand, passing more than 50% of the ethylene-containing feedstock to the first catalyst zone tends to increase the deactivation rate of the catalyst in the first catalyst zone. Another disadvantage of skewing the injection of ethylene-containing feedstock in favor of the first catalyst zone is that more exothermic reactions occur in the first catalyst zone. As a result, and in order to adequately and safely dissipate the greater heat release and the higher temperature rise, the first catalyst zone often becomes more complex mechanically and more expensive to build.

As mentioned previously, in its broadest embodiment this invention is an alkylation process having two catalyst zones, with a zeolite beta catalyst in the first catalyst zone and a zeolite Y catalyst in the second catalyst zone. This invention, however, is not limited to a process having merely one pair of catalyst zones. This invention includes embodiments wherein pairs of catalyst zones are connected in parallel or in series with each other. For example, in one embodiment of this invention that uses four catalyst zones, two pairs of catalyst zones are connected in parallel. The benzene-containing feedstock is divided into two portions, with one portion passing to one pair of catalyst zones and the other portion passing to the other pair of catalyst zones. The term portion as used herein may refer to an aliquot portion or to a non-aliquot portion. A portion of the ethylene-containing feedstock is passed to the each of the four zones. Within each pair of catalyst zones, a portion of the effluent of the first catalyst zone passes to the second catalyst zone. Portions of the effluents from both second catalyst zones then combine to form combined effluent from which ethylbenzene is recovered. Of course, this invention is not limited to the number of pairs of catalyst zones that may be connected in a parallel flow arrangement such as the embodiment just described.

In another embodiment of this invention that uses four catalyst zones, two pairs of catalyst zones are connected in series. In this embodiment, the entire benzene-containing feedstock passes to the first of two pairs of catalyst zones. A portion of the ethylene-containing feedstock is passed to each of the four catalyst zones. Within the first pair of catalyst zones, the benzene-containing feedstock enters the first catalyst zone and a portion of the effluent of the first catalyst zone passes to the second catalyst zone. A portion of the effluent of the second catalyst zone of the first pair of catalyst zones passes to the first catalyst zone of the second pair. Within the second pair, a portion of the effluent of the first catalyst zone passes to the second catalyst zone. Ethylbenzene is then recovered from the effluent of the second catalyst zone of the second pair. This invention is not limited to the number of pairs of catalyst zones that may be connected in such a series flow arrangement. This invention also includes embodiments in which pairs of catalyst zones are connected in any combination of series flow or parallel flow arrangements.

Where two pairs of catalyst zones are connected in a parallel or series flow arrangement as just described, the previous description of skewed injection of the ethylene-containing feedstock applies to each pair of catalyst zones. Thus, with two pairs of catalyst zones, generally from 10% to 100% of the total ethylene-containing feedstock that passes to each pair of catalyst zones passes to the first catalyst zone of each pair of catalyst zones. The remainder, if any, which is generally from 0% to 90% of the total ethylene-containing feedstock, passes to the second catalyst zone of each pair of catalyst zones. In a preferred embodiment of this invention, two pairs of catalyst zones are connected in a series flow arrangement as described in the previous paragraph, 50% of the total ethylene-containing feedstock passes to each pair of catalyst zones, 67% of the total ethylene-containing feedstock to each pair of catalyst zones passes to the first catalyst zone of each pair, and 33% of the total ethylene-containing feedstock to each pair of catalyst zones passes to the second catalyst zone of each pair. Thus, with respect to the total ethylene-containing feedstock that passes to both pairs of catalyst zones, 33.3% of the total passes to the first zone of the first pair, 16.7% of the total passes to the second zone of the first pair, 33.3% of the total passes to the first zone of the second pair, and 16.7% of the total passes to the second zone of the second pair.

One consequence of ethylene injection into one or more catalyst zones, other than the first catalyst zone, in a series flow arrangement of two or more catalyst zones is that the phenyl/ethyl ratio tends to decrease in each catalyst zone into which ethylene is injected. Thus, in the series flow arrangements described in the previous two paragraphs that consist of four catalyst zones, each with ethylene injection, the phenyl/ethyl ratio is greatest in the first catalyst zone, the phenyl/ethyl ratio in the second catalyst zone in series behind the first catalyst zone is second greatest, the phenyl/ethyl ratio in the third catalyst zone in series behind the second catalyst zone is third greatest, and the phenyl/ethyl ratio in the fourth catalyst zone in series behind the third catalyst zone is the least. In such an arrangement, it is common that the phenyl/ethyl ratio in the third catalyst zone is less than one-half of the phenyl/ethyl ratio in the first catalyst zone, and the phenyl/ethyl ratio in the fourth catalyst zone is less than one-half of the phenyl/ethyl ratio in the second catalyst zone. It is also common in such an arrangement that the alkylation temperature in the first catalyst zone is the same as the alkylation temperature in the third catalyst zone, and that the alkylation temperature in the second catalyst zone is the same as that in the fourth catalyst zone.

The first catalyst for the present invention may be one of a class of aluminosilicate molecular sieves known as zeolites. The zeolitic molecular sieves suitable for use in the first catalyst of the present invention are crystalline aluminosilicates which in the calcined form may be represented by the general formula:

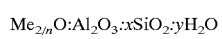

$$Me_{2/n}O:Al_2O_3:xSiO_2:yH_2O$$

where Me is a cation, n is the valence of the cation, x has a value of from about 5 to 100, and y has a value of from about 2 to 10. Detailed descriptions of zeolites may be found in D. W. Breck, Zeolite Molecular Sieves, John Wiley and Sons, New York 1974, and in other standard references. Suitable zeolites for the first catalyst are zeolite beta as disclosed in U.S. Pat. Nos. 4,891,458 and 5,081,323, the teachings of which are incorporated herein by reference, and a steamed and ammonium exchanged zeolite beta as disclosed in U.S. Pat. No. 5,522,984, the teachings of which are incorporated herein by reference. It is believed that mordenite and zeolite omega can also be suitable first catalysts for this invention.

A preferred zeolite for use as the first catalyst in this invention is a surface-modified zeolite beta which results from acid washing of a templated native zeolite beta. That is, the formation of the surface-modified zeolite beta starts with a templated beta where the template is, for example, a tetraalkylammonium salt, such as tetraethylammonium salt. It is critical to acid wash a templated zeolite beta in order to protect the internal sites of the zeolite and to prevent dealumination. The templated zeolite beta is treated with a strong acid at a pH between about 0 up to about 2, although a pH under 1 is preferred. Acids which may be used include nitric acid, sulfuric acid, phosphoric acid, and so forth. For example, a weak, 0.01 molar nitric acid may be used in conjunction with ammonium nitrate to perform the acid wash, although substantially higher concentrations, up to about 20 weight percent nitric acid, are preferred. Nitric acid is a preferred acid since it is a non-complexing acid and therefore does not encourage dealumination. Treatment of the templated zeolite beta with strong acid may be effected over the temperature range between about 20° C. up to about 125° C. It is important that acid washing be done under conditions not so severe as to effect dealumination.

The time over which acid washing is conducted in preparing the preferred zeolite for the first catalyst is quite temperature dependent. It is critical in the formation of the surface-modified zeolite beta that there be no significant bulk dealumination of the zeolite. Thus, as a general statement it can be said that acid washing should be done for a time insufficient to effect dealumination. For example, using 0.01 molar nitric acid and circa 40% ammonium nitrate at 70° C., contact times of 2–3 hours are found adequate to modify the environment of surface aluminum without causing significant bulk dealumination. Using circa 15% nitric acid with ammonium nitrate to treat a circa 25 weight percent slurry at 85° C., a 90-minute treatment is effective. The dependent variables in acid washing include acid concentration, slurry concentration, time and temperature, and suitable conditions at which surface-modified zeolite beta can be prepared without significant bulk dealumination are readily determined by the skilled artisan.

Next the template is removed by calcination at temperatures in the range of 550–700° C. Calcination conditions are well known in the art and need not be elaborated upon here. It also needs to be mentioned that powdered zeolite itself is not usually used as the first alkylation catalyst. Therefore, in the more usual case after the templated zeolite beta is acid washed it is mixed with a conventional binder, extruded, and the extrudate is ultimately calcined. But the critical portion of the preparation of the preferred zeolite for the first catalyst is the acid wash of the templated beta according to the foregoing description. Acid washing a calcined (i.e., non-templated) zeolite beta does not afford the surface-modified material of the preferred zeolite for the first catalyst.

It has been found that after treatment as described above the surface aluminum atoms are chemically modified. It has been hypothesized that the modification is in the form of replacement of strong acid sites at the catalyst surface by weaker acid sites. What has been definitely observed is that the surface aluminums of the preferred modified zeolite beta have 2p binding energies as measured by x-ray photoelectron spectroscopy of at least 74.8 electron volts. Further information on surface-modified zeolite beta resulting from acid washing of a templated native zeolite beta may be found in U.S. Pat. No. 5,723,710, the teachings of which are incorporated herein by reference.

The second catalyst normally comprises a zeolitic or nonzeolitic molecular sieve composited with a porous, inorganic refractory oxide matrix or binder. The term "nonzeolitic" as used herein refers to molecular sieves whose frameworks are not formed of substantially only silica and alumina tetrahedra such as the framework present in ZSM-5 type zeolites, Y zeolites, and X zeolites.

Examples of porous inorganic refractory oxide components which can be used as the binder or matrix for the second catalyst include alumina, gallia, thallia, titania, zirconia, beryllia, silica, silica-alumina, silica-magnesia, magnesia, silica-titania, other such combinations and the like. Examples of nonzeolitic crystalline molecular sieves which may serve as the active alkylation component of the catalyst include silicoaluminophosphates, aluminophosphates, ferrosilicates, chromosilicates, borosilicates, and crystalline silicas such as silicalite. The zeolitic crystalline molecular sieves which can be used as the active alkylation component of the second catalyst may be selected from the group of Y zeolites, fluorided Y zeolites, X zeolites, zeolite beta, zeolite L, zeolite omega, and modifications of such zeolites. In general, the second alkylation catalyst will contain between about 2 and about 98 weight percent molecular sieve, preferably between about 50 and about 95 weight percent, while the amount of binder or matrix in the catalyst will range between about 2 and about 98 weight percent, preferably between about 5 and about 50 weight percent.

The most preferred molecular sieve for use as the active alkylation component of the second alkylation catalyst are Y zeolites. U.S. Pat. No. 3,130,007, the disclosure of which is hereby incorporated by reference in its entirety, describes Y-type zeolites having an overall silica-to-alumina mole ratio between about 3.0 and about 6.0, with a typical zeolite Y having an overall silica-to-alumina mole ratio of about 5.0. It is also known that Y-type zeolites can be produced, normally by dealumination, having an overall silica-to-alumina mole ratio above 6.0. Thus, for purposes of this invention, a zeolite Y is one having the characteristic crystal structure of a zeolite Y, as indicated by the essential X-ray powder diffraction pattern of zeolite Y, and an overall silica-to-alumina mole ratio above 3.0, and includes Y-type zeolites having an overall silica-to-alumina mole ratio above 6.0.

A preferred zeolite Y for use as the molecular sieve component of the second alkylation catalyst is one produced by (1) first ammonium exchanging a zeolite Y to a sodium content between about 0.6 and 5.0 weight percent, calculated as $Na_2O$; (2) calcining the ammonium-exchanged zeolite at a temperature between about 600° F. and 1650° F. (316° C. and 899° C.) in the presence of steam at a water vapor partial pressure of at least 0.2 psi(a) (1.4 kPa(a)), preferably above about 2.0 psi(a) (13.8 kPa(a)), and most preferably between about 5.0 and about 15 psi(a) (34.5 and 103.4 kPa(a)), to reduce the unit cell size of the ammonium-exchanged zeolite to a value in the range between about 24.40 and 24.64 Angstroms, and then (3) ammonium exchanging the steam calcined zeolite to replace at least 25 percent of the residual sodium ions and obtain a zeolite product of less than about 1.0 weight percent sodium, preferably less than about 0.6 weight percent sodium, and most preferably below about 0.2 weight percent sodium, calculated as $Na_2O$. Such a zeolite Y is highly stable and maintains a high activity. The zeolite is described in detail in U.S. Pat. No. 3,929,672, the disclosure of which is hereby incorporated by reference in its entirety. The same or a substantially similar zeolite is sold by UOP as LZY-82 zeolite.

Although the shape of the second catalyst may be cylindrical, it is normally preferred that the second catalyst have a tri-lobe shape similar to the shape shown in FIGS. 8 and 8A of U.S. Pat. No. 4,028,227, the disclosure of which is hereby incorporated by reference in its entirety. It is normally desired that the second catalyst particles have a surface-to-volume ratio greater than that of particles in the shape of a cylinder and preferably in the range between about 85 and about 160 reciprocal inches (3.3 and 6.3 reciprocal mm). Normally, the length of the second catalyst particle ranges between about 0.01 and 0.25 inch (0.25 and 6.4 mm) and the diameter between about 0.03 and 0.08 inch (0.76 and 2.0 mm). The preferred shapes of the catalyst particles are described in U.S. Pat. No. 4,185,040, the disclosure of which is hereby incorporated by reference in its entirety.

FIG. 1 illustrates an embodiment of the invention for the production of ethylbenzene. For clarity and simplicity, some items associated with the operation of the process have not been shown. These items include flow and pressure control valves, pumps, heat exchangers, temperature and pressure monitoring systems, reactor internals, etc., which may be of customary design. FIG. 1 is not intended to limit the scope of the present invention as set forth in the claims.

Referring now to FIG. 1, fresh and/or recycle benzene flows through a line 14, receives ethylene from a line 12, and enters the first alkylation reactor 50 through a line 16. Alkylation reactor 50 houses two alkylation beds, 10 and 20, which are in series. Bed 10 contains a zeolite beta alkylation catalyst and bed 20 contains a zeolite Y alkylation catalyst. The effluent from bed 10 continues to flow through reactor 50. Line 18 supplies ethylene to reactor 50, where it combines with the effluent of bed 10 and contacts the catalyst in the bed 20. The effluent of bed 20 leaves reactor 50 and flows through a line 22 and is cooled by indirect heat exchanger 24. Exchanger 24 removes some of the exothermic heat of the alkylation reaction. The cooling medium of heat exchanger 24, which receives heat from the effluent stream, may be any suitable cool stream, such as cooling water, ambient air, or the fresh or recycle benzene that flows through the line 14.

The cooled effluent flows from exchanger 24 via a line 26, combines with ethylene flowing in a line 28, and enters via a line 32 into an alkylation reactor 60. Alkylation reactor 60 houses two alkylation beds, 30 and 40, which are in series. Bed 30 contains a zeolite beta alkylation catalyst and bed 40 contains a zeolite Y alkylation catalyst. Thus, the line 32 passes a mixture of ethylene and cooled reactor effluent into the reactor 60, where it contacts the catalyst in the bed 30. The effluent of bed 30 continues to flow through reactor 60, combines with ethylene for bed 40 which enters through a line 34, and contacts the catalyst in bed 40. Reaction zone effluent from alkylation bed 40 flows from reactor 60 via a line 36 to conventional separation facilities, which are not shown.

The beneficial operation of this invention will be further described in the context of several examples that exemplify the alkylation of ethylene with benzene to produce ethylbenzene. The Examples are based on engineering calculations and actual operating experience with similar processes. In describing these examples, valves, pumps, feeders, instruments, and heat exchangers other than those necessary for an understanding and appreciation of the invention have been omitted.

EXAMPLES

Examples 1–3 are illustrative of a preferred first catalyst for this invention.

Example 1

Preparation of acid washed zeolite beta. To a solution of 1428 grams ammonium nitrate in 3224 grams distilled water was added 932 grams of 70 weight percent nitric acid and the mixture was heated to 85° C. A dry weight of 1416 grams of commercial zeolite beta, $SiO_2$ 92.2 wt-%, $Al_2O_3$ 7.0 wt-%, LOI 24.3 wt-%, and $N_2$ BET 672 m²/g, was added and this mixture was stirred at 85° C. for 90 minutes. The slurry was filtered and washed using 10 liters of distilled water and then dried at 100° C. for 16 hours. After drying, the material was calcined at 650° C. for 3 hours in air. Analyses of this sample showed 91.7 wt-% $SiO_2$, 6.1 wt-% $Al_2O_3$, and a molar ratio $SiO_2/Al_2O_3$ of 25.5. The sample was examined by x-ray photoelectron spectroscopy (XPS) to determine binding energies, as well as the surface silicon: aluminum atomic ratio. The results are summarized in Table 1.

TABLE 1

| Peak | |
|---|---|
| Binding Energies (eV) | |
| Al2p | 75.20 |
| Si2p | 103.30 |
| O 1s | 532.43 |
| Surface Concentrations (atomic %) | |
| Al | 1.93 |
| Si | 29.91 |
| Si/Al (bulk) | ≈13 |
| Si/Al (XPS) | 16 |

Example 2

Preparation of catalyst containing acid washed zeolite beta. To a solution of 50 lb (22.68 kg) ammonium nitrate in water was added 12.6 lb (5.71 kg) nitric acid and the mixture was heated to 185° F. (85° C.). A dry weight of 50 lb (22.68 kg) of commercial zeolite beta granules, which had 92.78 wt-% $SiO_2$, 6.68 wt-% $Al_2O_3$, 19.6 wt-% LOI at 1832° F. (1000° C.), and 665 m²/g surface area (1 pt), was passed through a pin mill to obtain uniform powder. The powder was added to the mixture, and the resulting slurry, which contained 9.3 wt-% solids, was mixed at 185° F. (85° C.) for 1 hour. The slurry was filtered and washed using 1095 lb (496.7 kg) of water, and the cake was dried in air overnight. The air-dried cake was placed in trays and oven dried at 200° F. (93° C.) to equilibrium.

A dry weight of 12 lb (5.44 kg) of a mull batch was made by combining the oven-dried cake, peptizable alumina, and non-peptizable alumina filler in relative dry weight proportions of 70 wt-% oven-dried cake, 20 wt-% peptizable alumina, and 10 wt-% non-peptizable alumina filler. The mull batch was peptized using 0.25 lb of nitric acid per lb of alumina being peptized, with an organic burnout agent added to the mull batch as 5 wt-% of the total dry mull batch weight for purposes of improving porosity. The peptized mull batch, which had 46.5 wt-% LOI at 1832° F. (1000° C.), was extruded into 1/16 in (1.6 mm) extrudates, which were then placed in trays and oven-dried at 200° F. (93° C.).

The dried extrudates were calcined in a rotary kiln at a maximum bed temperature of about 1250° F. (675° C.) in air. Analyses of a sample of the resulting catalyst showed 62.82 wt-% $SiO_2$, and 37.09 wt-% $Al_2O_3$, with both results corrected for as-received LOI and normalized.

Example 3

Alkylation of benzene with ethylene using catalyst containing acid washed zeolite beta. 40 cc of the catalyst described in Example 2 were loaded into a reactor to form a bed 5/8 in (15.9 mm) in diameter and 10.5 in (266.7 mm) long. The catalyst was activated for 12 hours by passing a stream of benzene over the catalyst at 464° F. (240° C.), 550 psi(g) (3792 kPa(g)), and 7 WHSV benzene. Temperature was adjusted to the desired run temperature and the feed switched to a blend of 0.45 WHSV ethylene and 7 WHSV benzene. The resulting molar ratio of benzene per ethylene was 6.18. The position of the maximum temperature (due to the exothermic reaction) in the bed was noted. Deactivation was determined by noting the position of the maximum temperature after a suitable interval of time (e.g., 48 hours) at test conditions. Deactivation is calculated by taking the difference in these two positions (in inches), dividing by the bed length (in inches), and then dividing by the time interval (in hours). The results are multiplied by 100% to give a deactivation rate in percent of catalyst bed/hour. The catalyst was tested at 482° F. (250° C.), and the deactivation rate was 0.0055% per hour.

Example 4 is illustrative of a preferred second catalyst for use in this invention.

Example 4

Alkylation of benzene with ethylene using catalyst containing zeolite Y. 40 cc of 1/16 in (1.6 mm) tri-lobe pellets containing 80 wt-% LZY-82 and 20 wt-% alumina were loaded into a reactor to form a bed 5/8 in (15.9 mm) in diameter and 10.75 in (273.1 mm) long. The catalyst was activated for 12 hours by passing a stream of benzene over the catalyst at 464° F. (240° C.), 550 psi(g) (3792 kPa(g)), and 7 WHSV benzene. Temperature was adjusted to the desired run temperature and the feed switched to a blend of 0.45 WHSV ethylene and 7 WHSV benzene. The resulting molar ratio of benzene per ethylene was 6.31. The position of the maximum temperature (due to the exothermic reaction) in the bed was noted. Deactivation was determined by the method described in Example 3. The catalyst was tested at 482° F. (250° C.), and the deactivation rate was 0.0596% per hour.

Example 5 shows that, in the alkylation of benzene with ethylene in the presence of a catalyst containing zeolite beta, flux oil production increases as alkylation reactor outlet temperature increases.

Example 5

A sample of catalyst that is similar to that made in Example 2 was made according to a method that is similar to that described in Example 2. This sample, which was hydrated at a level of 14.8 wt-%, is referred to herein as Catalyst A.

A quantity of 0.110 lb (50 g) of Catalyst A was loaded into a reactor to form a bed that was 7.68 in (19.5 cm) in length. Ethylene having a purity of 99.9 vol-% and benzene were passed over the catalyst for approximately 89 days, and the bed effluent was analyzed for flux oil by gas chromatography. The operating pressure of the catalyst bed was 540 psi(g) (3726 kPa(g)). For purposes of this Example 5 and the following Example 6 only, flux oil is defined as approximately the sum of 20% of the tetraethylbenzene and 100% of the diphenylethane in the bed effluent.

During the period from day 30 to day 62, the molar ratio of benzene per ethylene was 20:1 and the reactor inlet temperature was gradually decreased from 478° F. (248° C.) on day 30 to 419° F. (215° C.) on day 62. The reactor outlet temperature gradually decreased from 502° F. (261° C.) on day 30 to 448° F. (231° C.) on day 62.

Figure 2:
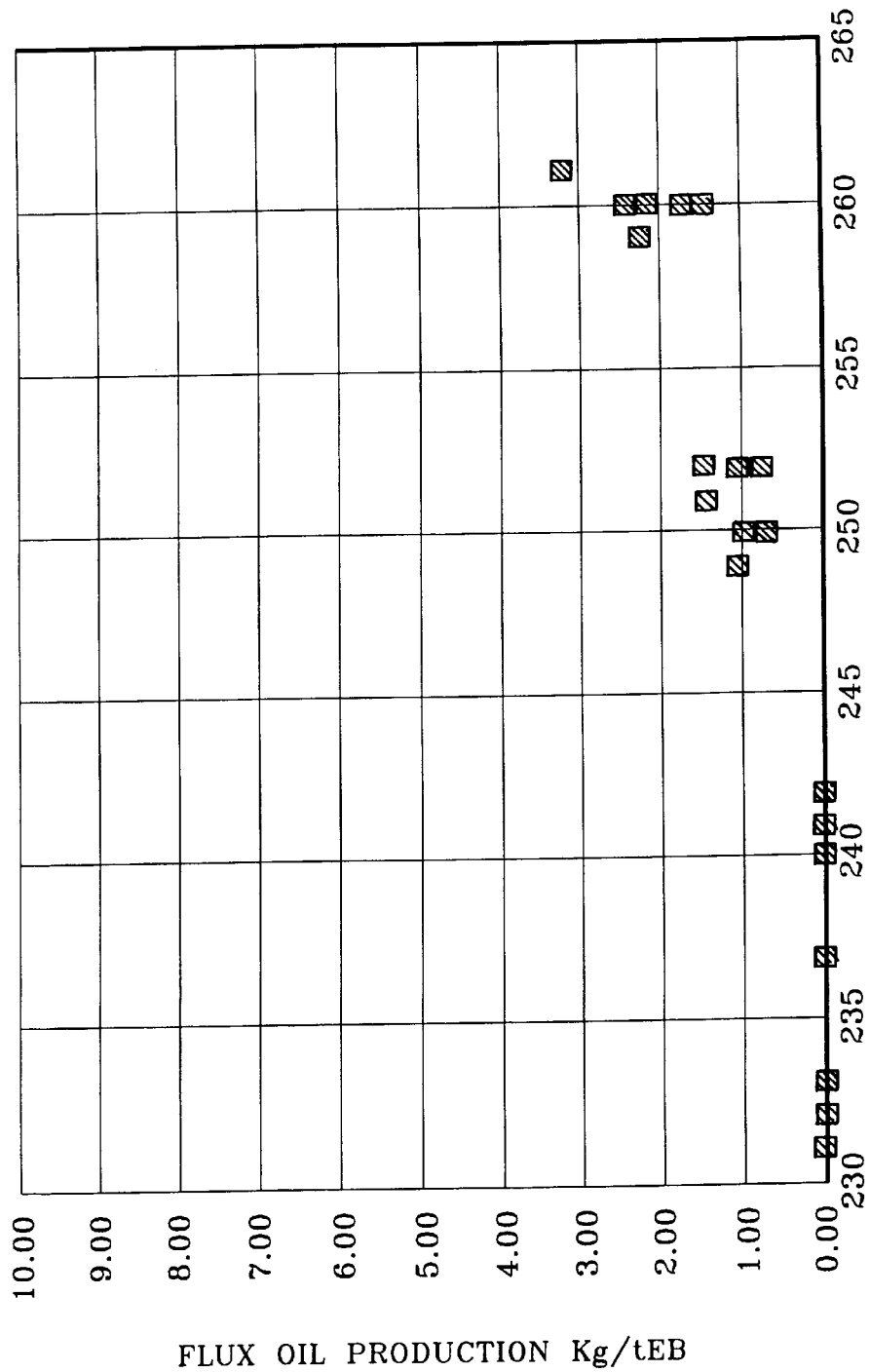
FIGS. 2 and 3 show flux oil production as a function of temperature in alkylating benzene with ethylene in the presence of beta type zeolite.

FIG. 2 demonstrates that during the period from day 30 to day 62, flux oil decreased with decreasing reactor outlet temperature at a benzene/ethylene ratio of 20:1. FIG. 2 shows flux oil production on the y-axis as a function of reactor outlet temperature on the x-axis during the period from day 30 to day 62. Flux oil production is presented in units of kilograms of flux oil produced per metric ton of ethylbenzene produced. Data points that show zero (0) flux oil production mean that the concentration in the bed effluent of each of the flux oil components is less than the limit of detection of the gas chromatograph.

During the period from day 62 to day 89, the molar ratio of benzene per ethylene was 18:1 and the reactor inlet temperature was gradually increased, ranging from about 417° F. (214° C.) on day 63 to 475° F. (246° C.) on day 84. The reactor outlet temperature gradually increased, ranging from 448° F. (231° C.) on day 63 to 502° F. (261° C.) on day 86.

Figure 3:
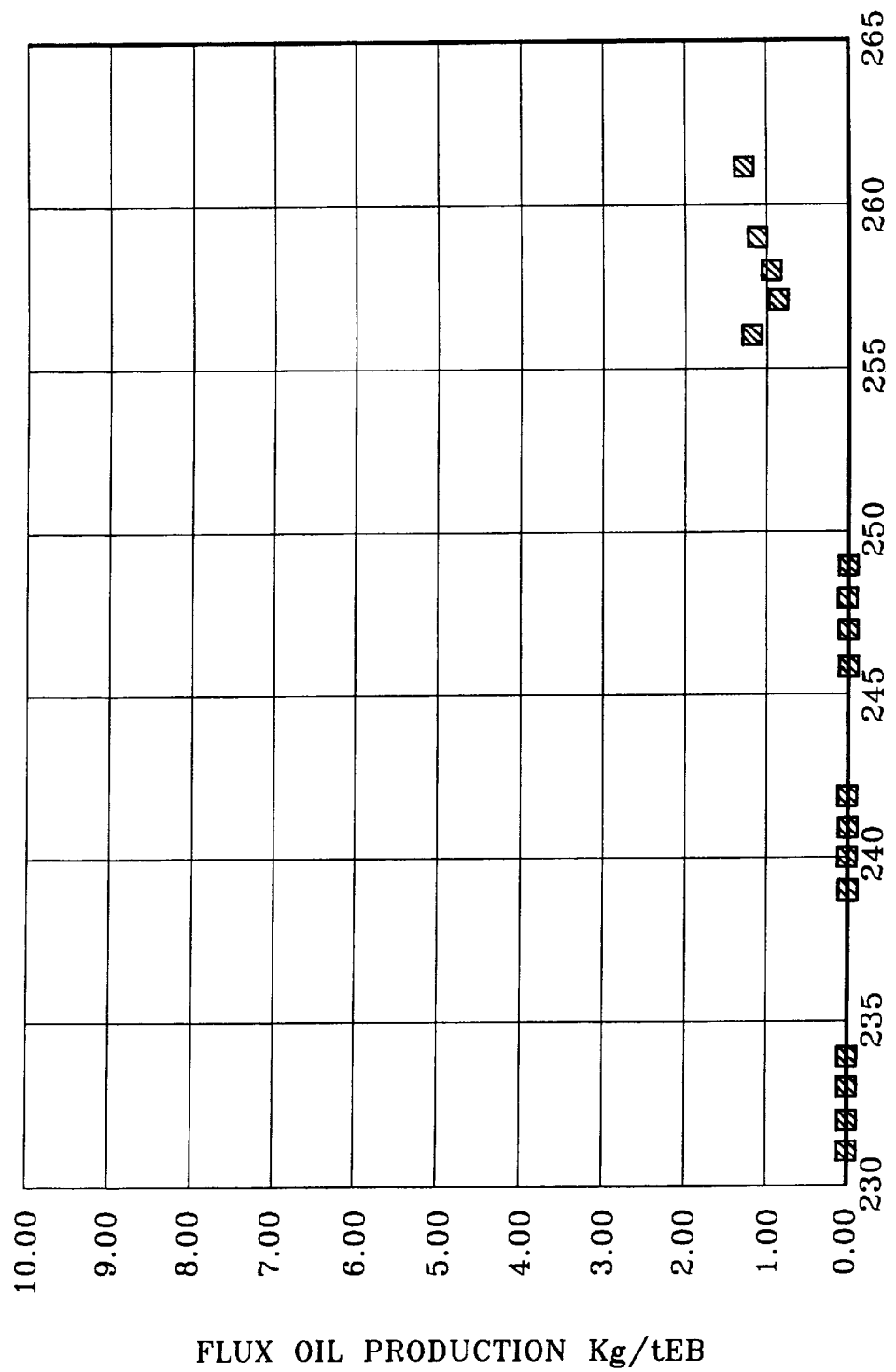

The data in FIG. 3, which are presented in the same manner as the data in FIG. 2, show that during the period from day 62 to day 89 and at a benzene/ethylene ratio of 18:1, flux oil increased with increasing reactor outlet temperature. Thus, the temperature dependence of flux oil production in the presence of Catalyst A at a benzene/ethylene ratio of 18:1 is similar, although somewhat less pronounced, than at 20:1. Results not shown from other tests with Catalyst A at benzene/ethylene ratios of 16:1 and of 12:1 also indicate an analogous temperature dependence.

Example 6 shows that, in the alkylation of benzene with ethylene in the presence of a catalyst containing zeolite Y, flux oil production decreases as alkylation reactor outlet temperature increases.

Example 6

A sample of catalyst that is similar to that made in Example 4 was made according to a method that is similar to that described in Example 4. This sample, which was hydrated at a level of 21.0 wt-%, is referred to herein as Catalyst B.

A quantity of 0.110 lb (50 g) of fresh Catalyst B was loaded into a reactor to form a bed that was 8.27 in (21.0 cm) in length. Ethylene having a purity of 99.9 vol-% and benzene were passed over the catalyst for approximately 68 days, and the bed effluent was analyzed for flux oil by gas chromatography. The operating pressure of the catalyst bed was 540 psi(g) (3726 kPa(g)). For purposes of this Example 6, flux oil has the same definition as that given in Example 5.

Figure 4:
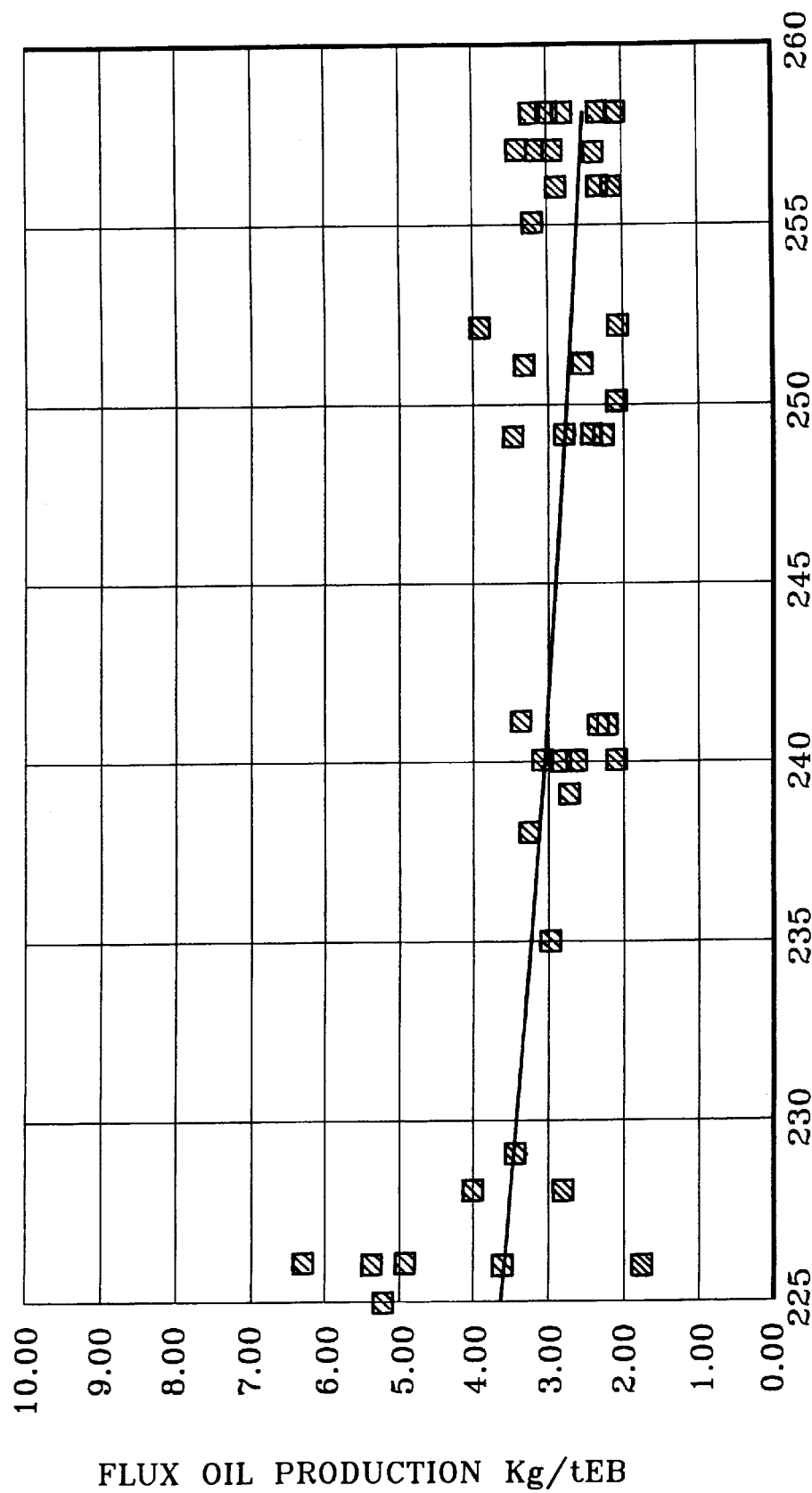
FIGS. 4 and 5 show flux oil production as a function of temperature in alkylating benzene with ethylene in the presence of Y type zeolite.

During the period from day 1 to day 55, the molar ratio of benzene per ethylene was 20:1 and the reactor inlet temperature was gradually decreased from 477° F. (247° C.) on day 1 to 399° F. (204° C.) on day 55. The reactor outlet temperature gradually decreased from 498° F. (259° C.) on day 1 to 437° F. (225° C.) on day 55. FIG. 4, which presents the data during the period from day 1 to day 55 in the same manner as in FIG. 2, shows flux oil increased with decreasing reactor outlet temperature.

During the period from day 55 to day 68, the molar ratio of benzene per ethylene was 18:1 and the reactor inlet temperature was gradually increased from 401° F. (205° C.) on day 55 to 430° F. (221° C.) on day 68. The reactor outlet temperature gradually increased, ranging from about 441° F. (227° C.) on day 57 to 468° F. (242° C.) on day 63.

Figure 5:
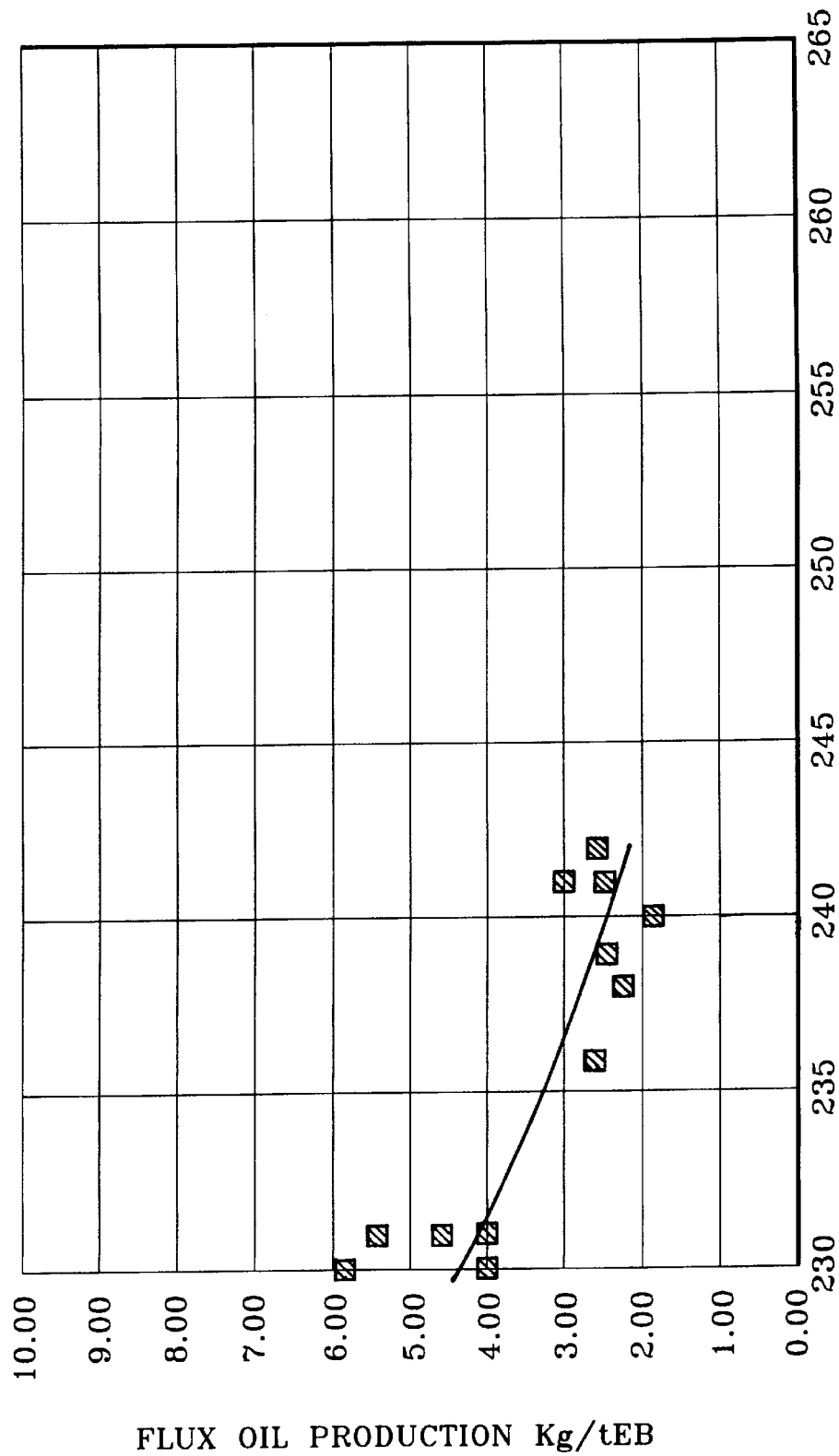

During the period from day 55 to day 68, flux oil decreased with increasing reactor outlet temperature, as demonstrated in FIG. 5. FIG. 5 depicts the data for the period from day 55 to day 68 at a benzene/ethylene ratio of 18:1 in the same manner as in FIG. 2. The temperature dependence of the flux oil production is much starker and more clearly apparent in FIG. 5 than in FIG. 4. It is believed that the explanation for this is that the dependence of flux oil production on temperature may be easier to observe in the presence of Catalyst B under the more severe conditions (i.e., 18:1 molar ratio of benzene per ethylene), because flux oil production increases as the molar ratio of benzene per ethylene decreases.

Example 7 exemplifies the relatively small quantity of flux oil that is produced in a commercial ethylbenzene unit that is an embodiment of this invention, and Example 8 exemplifies the relatively large quantity of flux oil that is produced in another commercial ethylbenzene unit that is typical of a prior art process.

As used in Examples 7 and 8, and with reference to FIG. 1 and Tables 2 and 3, the overall molar ratio of benzene per ethylene is defined as the moles of benzene entering per unit of time through the line 14 divided by the total number of moles of ethylene entering per unit of time through the lines 12, 18, 28, and 34. The nominal total ethylene weight hourly space velocity (WHSV) is defined as the weight of ethylene entering per hour through the lines 12, 18, 28, and 34, divided by the weight of catalyst in beds 10, 20, 30, and 40. The distribution of catalyst is defined as the weight of catalyst in a bed divided by the total weight of catalyst in beds 10, 20, 30, and 40, times 100. The distribution of ethylene injection is defined as the weight of ethylene injected per unit of time to a bed divided by the total weight of ethylene injected per unit of time to beds 10, 20, 30, and 40, times 100. Flux oil production is in units of kilograms of flux oil produced per metric ton of ethylbenzene produced.

Example 7

The flow scheme for this Example 7 is the same as that in FIG. 1. One catalyst, which is referred to herein as Catalyst C, was similar to the catalyst that was made in Example 2 and was made according to a method that is similar to that described in Example 2. Catalyst C was loaded into bed positions 10 and 30 as shown in FIG. 1. The other catalyst, which is referred to herein as Catalyst D, was similar to the catalyst that was made in Example 4 and was made according to a method that is similar to that described in Example 4. Catalyst D occupied bed positions 20 and 40 as shown in FIG. 1 and produced ethylbenzene commercially for about five years prior to its use for this Example.

The process of FIG. 1, with Catalyst C in bed positions 10 and 30 and with Catalyst D in bed positions 20 and 40, processed benzene-containing and ethylene-containing feeds and operated to produce ethylbenzene for 2–4 weeks. During that time, the inlet and outlet temperatures of the beds and the distribution of ethylene to the beds were adjusted to minimize flux oil production. Then data for three days of operation were collected and averaged, and these average data are presented in Table 2. The average flux oil production over this three-day test period was 6.3 kg of flux oil per metric ton of ethylbenzene produced.

TABLE 2

| | |
|---|---|
| Overall Molar Ratio of Benzene per Ethylene, mole/mole | 5.8 |
| Pressure, kg/cm$^2$(g) | 38.3 |
| Nominal Total Ethylene WHSV, hr$^{-1}$ | 0.30 |
| Type of Catalyst in Beds 10–40 | |
| Bed 10 | zeolite beta |
| Bed 20 | zeolite Y |
| Bed 30 | zeolite beta |
| Bed 40 | zeolite Y |
| Distribution of Catalyst in Beds 10–40, wt-% | |
| Bed 10 | 18 |
| Bed 20 | 32 |
| Bed 30 | 18 |
| Bed 40 | 32 |
| Distribution of Ethylene Injection to Beds 10–40, wt-% | |
| Bed 10 | 33.3 |
| Bed 20 | 16.7 |
| Bed 30 | 33.3 |
| Bed 40 | 16.7 |

TABLE 2-continued

| | |
|---|---|
| Approximate Bed Outlet Temperature, ° C. | |
| Bed 10 | 246 |
| Bed 20 | 259 |
| Bed 30 | 251 |
| Bed 40 | 262 |
| Flux Oil Production, kg/tEB | 6.3 |

Example 8

The flow scheme for this Example 8 is the same as that in FIG. 1. Catalyst E was similar to the catalyst that was made in Example 2 and was made according to a method that is similar to that described in Example 2. Catalyst E was loaded into bed positions 10, 20, 30, and 40 of FIG. 1.

The process of FIG. 1 with Catalyst E in all four bed positions processed benzene-containing and ethylene-containing feeds and operated to produce ethylbenzene for 2–4 weeks. During that time, the inlet and outlet temperatures of the beds and the distribution of ethylene to the beds were adjusted to minimize flux oil production. Then data for three days of operation were collected and averaged, and these average data are presented in Table 3. The average flux oil production over this three-day test period was 7.8 kg of flux oil per metric ton of ethylbenzene produced.

TABLE 3

| | |
|---|---|
| Overall Molar Ratio of Benzene per Ethylene, mole/mole | 6.1 |
| Pressure, kg/cm$^2$(g) | 38 |
| Nominal Total Ethylene WHSV, hr$^{-1}$ | 0.29 |
| Type of Catalyst in Each of Beds 10–40 | zeolite beta |
| Distribution of Catalyst in Each of Beds 10–40, wt-% | 25 |
| Distribution of Ethylene Injection to Beds 10–40, wt-% | |
| Bed 10 | 30 |
| Bed 20 | 20 |
| Bed 30 | 30 |
| Bed 40 | 20 |
| Approximate Bed Outlet Temperature, ° C. | |
| Bed 10 | 241 |
| Bed 20 | 257 |
| Bed 30 | 239 |
| Bed 40 | 255 |
| Flux Oil Production, kg/tEB | 7.8 |

Thus, Examples 7 and 8 illustrate the surprising decrease in flux oil production that occurs in a two-catalyst-zone alkylation process that uses zeolite beta and zeolite Y in comparison with the relatively high flux oil production in a single-catalyst-zone alkylation process that uses zeolite beta only. Even with the custom tailoring of conditions for the process of each Example 7 and 8 to reduce the amount of flux oil, the zeolite beta—zeolite Y combination produced over 20% less flux oil than the all zeolite beta operation. Furthermore, because zeolite Y is known to generally produce even more flux oil than zeolite beta, a two-catalyst-zone alkylation process that uses zeolite beta and zeolite Y would therefore be expected to produce much less flux oil than a single-catalyst-zone alkylation process that uses zeolite Y. Therefore, a two-catalyst-zone alkylation process that employs a first catalyst comprising a zeolite beta and a second catalyst comprising a zeolite Y demonstrates surprising yield improvements over a single-catalyst-zone system of either zeolite beta or zeolite Y.

What is claimed is:

1. A process for producing ethylbenzene comprising:
   a) contacting a first feed comprising benzene and ethylene with a first catalyst comprising zeolite beta in a first catalyst zone at first alkylation conditions to obtain a first effluent, and withdrawing the first effluent from the first catalyst zone at a first temperature; and
   b) contacting a second feed including at least a portion of the first effluent and comprising ethylene and benzene with a second catalyst comprising zeolite Y in a second catalyst zone at second alkylation conditions to obtain a second effluent comprising ethylbenzene, and withdrawing the second effluent from the second catalyst zone at a second temperature, wherein the second temperature is higher than the first temperature.

2. The process of claim 1 further characterized in that each of the first alkylation conditions and the second alkylation conditions comprise a pressure sufficient to maintain benzene in at least a partial liquid phase, a temperature of from about 212 to about 552° F., and a molar ratio of phenyl groups per ethyl group of from about 0.75:1 to about 25:1.

3. The process of claim 1 further characterized in that each of the first alkylation conditions and the second alkylation conditions comprise a weight hourly space velocity of ethylene of from 0.01 to 2.0 $hr^{-1}$ and a weight hourly space velocity of aromatics of from about 0.3 to about 480 $hr^{-1}$.

4. The process of claim 1 further characterized in that the second temperature is at least 45° F. higher than the first temperature.

5. The process of claim 1 further characterized in that the first effluent is cooled prior to the contacting of the first effluent with the second catalyst.

6. The process of claim 1 wherein the zeolite beta comprises a calcined, non-templated surface-modified zeolite beta characterized by having surface aluminum 2p binding energies, as measured by X-ray photoelectron spectroscopy, of at least 74.8 electron volts.

7. The process of claim 1 wherein the first catalyst zone and the second catalyst zone are housed in a common reactor vessel.

8. The process of claim 1 further characterized in that the second effluent is cooled to produce a cooled second effluent, the cooled second effluent and ethylene are contacted with a third catalyst comprising zeolite beta in a third catalyst zone at third alkylation conditions to obtain a third effluent, and the third effluent and ethylene are contacted with a fourth catalyst comprising zeolite Y in a fourth catalyst zone at fourth alkylation conditions to obtain a fourth effluent comprising ethylbenzene.

9. The process of claim 8 further characterized in that the first alkylation conditions comprise a first molar ratio of phenyl groups per ethyl group, the third alkylation conditions comprise a second molar ratio of phenyl groups per ethyl group that is less than one-half of the first molar ratio of phenyl groups per ethyl group, the third effluent is withdrawn from the third catalyst zone at a third temperature, and the third temperature is the same as the first temperature.

10. The process of claim 8 further characterized in that the second alkylation conditions comprise a first molar ratio of phenyl groups per ethyl group, the fourth alkylation conditions comprise a second molar ratio of phenyl groups per ethyl group that is less than one-half of the first molar ratio of phenyl groups per ethyl group, the fourth effluent is withdrawn from the fourth catalyst zone at a third temperature, and the third temperature is the same as the second temperature.

11. The process of claim 1 further characterized in that ethylene is added to the portion of the first effluent to form the second feed.

12. The process of claim 11 further characterized in that the quantity of ethylene that contacts the first catalyst is a first quantity, the quantity of ethylene that is added to the portion of the first effluent is a second quantity, and the first quantity is from 20 to 95% of the total of the first quantity and the second quantity.

13. The process of claim 1 further characterized in that the quantity of the first catalyst is a first quantity, the quantity of the second catalyst is a second quantity, and the first quantity is from about 10 to about 90% of the total of the first quantity and the second quantity.

* * * * *